US009017702B2

(12) United States Patent
Leskovar et al.

(10) Patent No.: US 9,017,702 B2
(45) Date of Patent: Apr. 28, 2015

(54) STABLE AQUEOUS FORMULATIONS COMPRISING POORLY WATER SOLUBLE ACTIVE INGREDIENTS

(75) Inventors: Denise Leskovar, Oplotnica (SI); Franc Vrecer, Straza pri Novem mestu (SI); Andrejka Kramar, Novo mesto (SI); Ivanka Kolenc, Novo mesto (SI); Ivan Gobec, Kresnice (SI); Helena Princ, Novo mesto (SI)

(73) Assignee: KRKA, D.D., Novo Mesto, Novo Mesto (SI)

( * ) Notice: Subject to any disclaimer, the term of this patent is extended or adjusted under 35 U.S.C. 154(b) by 0 days.

(21) Appl. No.: 13/808,663

(22) PCT Filed: Jul. 6, 2011

(86) PCT No.: PCT/EP2011/061419
§ 371 (c)(1),
(2), (4) Date: Jan. 7, 2013

(87) PCT Pub. No.: WO2012/004308
PCT Pub. Date: Jan. 12, 2012

(65) Prior Publication Data
US 2013/0171212 A1 Jul. 4, 2013

(30) Foreign Application Priority Data
Jul. 6, 2010 (EP) .................................. 10168532

(51) Int. Cl.
*A61K 9/00* (2006.01)
*A61K 47/00* (2006.01)
(Continued)

(52) U.S. Cl.
CPC ............... *A61K 47/38* (2013.01); *A61K 9/0095* (2013.01); *A61K 9/10* (2013.01); *A61K 47/32* (2013.01); *A61K 47/36* (2013.01); *A61K 47/02* (2013.01)

(58) Field of Classification Search
CPC ....... A61K 9/0095; A61K 9/10; A61K 47/02; A61K 47/36; A61K 47/38; A61K 47/32
USPC ............... 424/400, 439, 442; 514/770, 772.3, 514/772.6, 781
See application file for complete search history.

(56) References Cited

U.S. PATENT DOCUMENTS 5,455,037 A 10/1995 Sakai
5,458,879 A * 10/1995 Singh et al. ................... 424/400
(Continued)

FOREIGN PATENT DOCUMENTS

EP 0 727 996 8/1996
EP 1 214 052 6/2002
(Continued)

*Primary Examiner* — Blessing M Fubara
(74) *Attorney, Agent, or Firm* — Cozen O'Connor

(57) ABSTRACT

A formulation includes one or more active ingredients of poor water solubility for medical or non-medical use in the rearing of animals. The formulation is suitable for administration to the animals via their drinking water. It exhibits superior stability. The formulation comprises an active ingredient, a thickener combination and water, wherein the thickener combination comprises at least one thickener selected from the following groups A, B, C and D:

(A) cellulose derivatives, such as methyl cellulose, sodium carboxy methyl cellulose,
(B) non-cellulosic polysaccharide thickeners such as xanthan gums, Arabic gum,
(C) cross-linked polyacrylic acid polymers,
(D) hydrocolloidal hydrated silicates.

9 Claims, 1 Drawing Sheet

(51) Int. Cl.
*A23K 1/17* (2006.01)
*A61K 47/30* (2006.01)
*A61K 47/32* (2006.01)
*A61K 47/38* (2006.01)
*A61K 9/10* (2006.01)
*A61K 47/36* (2006.01)
*A61K 47/02* (2006.01)

(56) References Cited

U.S. PATENT DOCUMENTS

| | | | |
|---|---|---|---|
| 5,538,989 | A | 7/1996 | Kyle |
| 6,294,186 | B1 | 9/2001 | Beerse et al. |
| 2002/0146443 | A1* | 10/2002 | Gers-Barlag et al. ......... 424/401 |
| 2003/0206949 | A1* | 11/2003 | Parikh et al. ................. 424/465 |
| 2007/0048338 | A1 | 3/2007 | Ladd |
| 2007/0166372 | A1 | 7/2007 | Huang et al. |
| 2009/0062362 | A1 | 3/2009 | Ekhart et al. |

FOREIGN PATENT DOCUMENTS

| | | |
|---|---|---|
| WO | WO 02/41847 | 5/2002 |
| WO | WO 2004/050021 | 6/2004 |
| WO | WO 2005/018530 | 3/2005 |
| WO | WO 2007/026261 | 3/2007 |
| WO | WO 2007/038949 | 4/2007 |
| WO | WO 2007/102946 | 9/2007 |
| WO | WO 2007/144362 | 12/2007 |
| WO | WO 2008/012495 | 1/2008 |
| WO | WO 2010/011289 | 1/2010 |
| WO | WO 2010/045700 | 4/2010 |
| WO | WO 2010/063988 | 6/2010 |

* cited by examiner

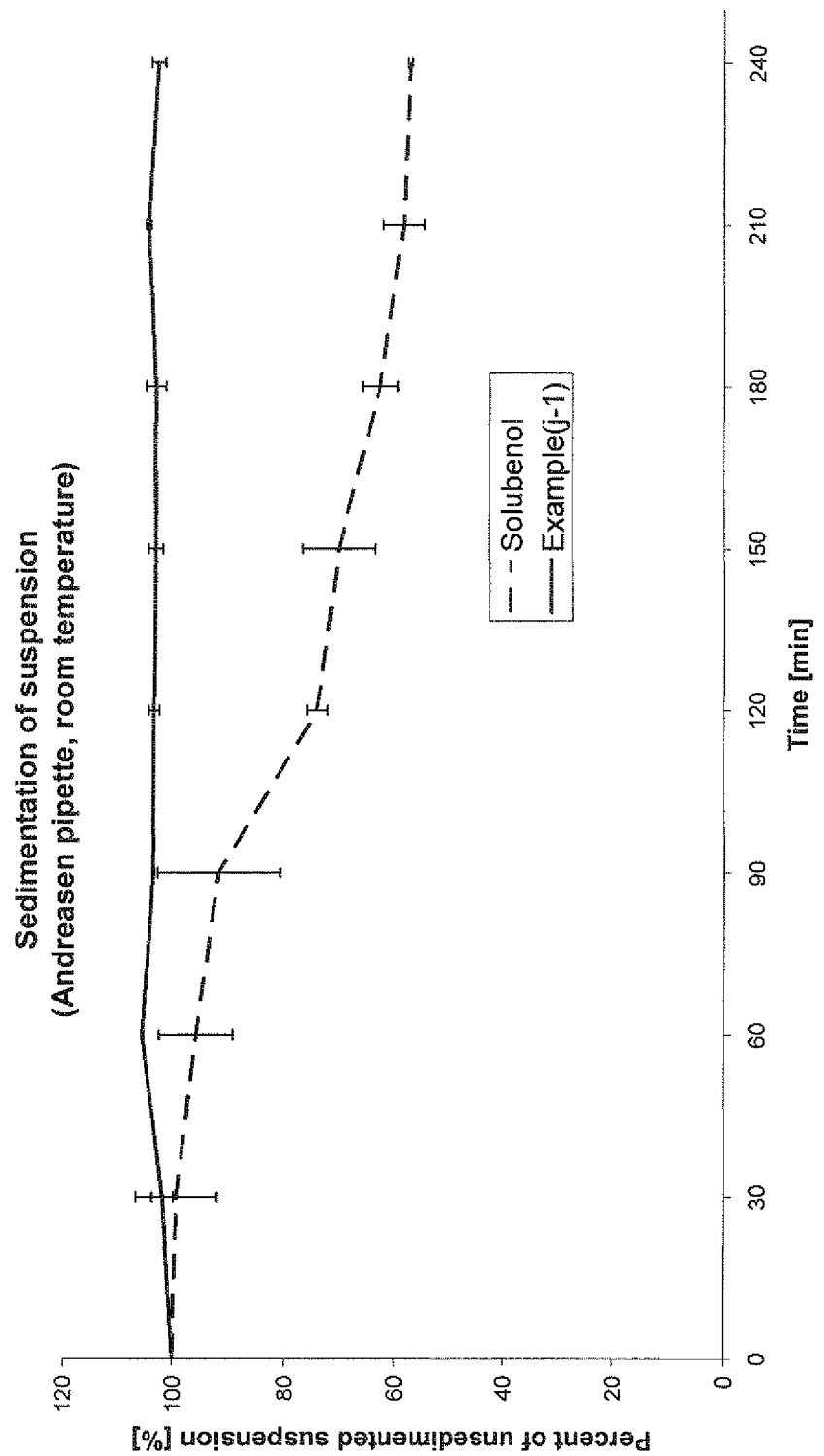

STABLE AQUEOUS FORMULATIONS COMPRISING POORLY WATER SOLUBLE ACTIVE INGREDIENTS

PRIORITY CLAIM

This is a U.S. national stage of application No. PCT/EP2011/061419, filed on Jul. 6, 2011. Priority is claimed on the following application: Country: Europe, Application No.: 10168532.9, Filed: Jul. 6, 2010, the content of which is incorporated herein by reference.

TECHNICAL FIELD OF THE INVENTION

The present invention relates to formulations for administering water poorly soluble drugs to animals in drinking water. In particular, the present invention relates to a stable formulation which is free of water immiscible liquids and free of surfactants which are the most common approaches in the prior art formulations to be administered via the drinking water.

BACKGROUND OF THE INVENTION

EP 1 214 052 A discloses suspoemulsions comprising a mixture of active ingredient and water-immiscible liquid, preferably sunflower oil, and one of stabilizing agent belonging to group of emulsifiers, surfactants, thickeners, anti-oxidants and antimicrobial agent.

EP 0 727 996 A discloses aqueous suspensions of fenbendazol, non-ionic surface active agent and preservative.

WO 2007/144362 A discloses formulations for drinking water administration comprising a Tween-type surfactant and an active ingredient having average particle size below 450 nm.

WO 2010/045700 A discloses formulations comprising 0.5-15% benzimidazole type active agent, 0.2-10% alkane glycoles or polyalkane glycol, 0.5-15% of surfactant selected from non ionic polyethylene sorbitan monooleate, 0.01-5% emulsifier selected from lactose, sucrose, mannitol, xanthan gum, 0.01-5% stabilizer from the group of antimicrobials.

WO 2010/011289 A provides a formulation comprising an oil, surfactant, co-surfactant, and dipolar protic solvent.

In spite of the above teachings, there is still demand for veterinary compositions comprising water-insoluble active ingredients in an aqueous dispersed form, which exhibit an increased stability.

The present invention was made to meet this demand. Thus, the present invention provides particularly stable veterinary compositions comprising active ingredients with limited solubility in water in an aqueous dispersed form. In particular, these compositions exhibit the following benefit: The choice of ingredients permits an economical preparation and formulation which is less risky to health. Further advantages are chemical and physical stability of the formulation, stability of the secondary preparation after dilution of the formulation with water in terms of sedimentation and segregation.

SUMMARY OF THE INVENTION

The above objective is accomplished in the present invention by providing a formulation comprising an active ingredient, a thickener combination and water, wherein the thickener combination comprises at least one thickener selected from the following groups A, B, C and D:

(A) cellulose derivatives, such as methyl cellulose, sodium carboxy methyl cellulose,
(B) non-cellulosic polysaccharide thickeners such as xanthan gums, Arabic gum,
(C) cross-linked polyacrylic acid polymers, and
(D) hydrocolloidal hydrated silicates.

The present invention furthermore provides methods for manufacturing the formulations of the invention. Said methods are characterized by the following features: Process of manufacturing the formulation according to the present invention, comprising the step of forming a mixture of thickener combination and water, followed by combination of this mixture with the active ingredient.

Further aspects of the present invention relate to the use of the formulation of the invention in rearing animals, preferably farm animals such as pigs, poultry (e.g., chickens, laying hens, breeders and pullets), cattle, turkeys, fish. Such uses include medical and non-medical aspects. For instance, in a medical aspect, the present invention relates to the formulations of the present invention for use in the treatment or prevention of microbial or parasitic infections (e.g. helminthosis), hypovitaminoses and other conditions. Non-medical aspects of the present invention include the use of the formulations of the present invention for increasing growth rate of the animals.

BRIEF DESCRIPTION OF THE FIGURE

FIG. 1 shows a graphical representation of the results of a comparative stability test employing the Andreasen pipette technique.

DETAILED DESCRIPTION OF THE INVENTION

(a) Definitions

Unless expressly specified otherwise, the term "comprising" is used in the context of the present application to indicate that further members may optionally be present in addition to the members of the list introduced by "comprising". It is, however, contemplated as a specific embodiment of the present invention that the term "comprising" encompasses the possibility of no further members being present, i.e. for the purpose of this embodiment "comprising" is to be understood as having the meaning of "consisting of".

The following detailed description discloses specific and/or preferred variants of the individual features of the invention. The present invention also contemplates as particularly preferred embodiments those embodiments, which are generated by combining two or more of the specific and/or preferred variants described for two or more of the features of the present invention.

Unless expressly specified otherwise, all indications of relative amounts in the present application are made on a weight/weight basis. Indications of relative amounts of a component characterized by a generic term are meant to refer to the total amount of all specific variants or members covered by said generic term. If a certain component defined by a generic term is specified to be present in a certain relative amount, and if this component is further characterized to be a specific variant or member covered by the generic term, it is meant that no other variants or members covered by the generic term are additionally present such that the total relative amount of components covered by the generic term exceeds the specified relative amount; more preferably no other variants or members covered by the generic term are present at all.

In the context of the present invention, the term "median particle size" is meant to refer to the volume mean diameter of the particles. The volume mean diameter is determined by laser light scattering using a Malvern-Mastersizer Apparatus MS 2000 equipped with Hydro G dispersion unit. Purified water is used as the dilution medium.

Unless expressly specified otherwise, all technical terms are used to have the generally accepted meaning as reflected in standard reference books such as Rompp Lexikon Chemie, Thieme Verlag, CD-ROM Version of 2006.

(b) Active Ingredient

The formulations of the present invention are for administration to drinking water of animals, preferably farm animals. These formulations comprise at least one active ingredient exhibiting a low solubility in water. Said one or more active ingredient(s) is/are preferably selected from anthelmintics, such as benzimidazoles (flubendazole, fenbendazole, thiabendazole, cambendazole, parbendazole, mebendazole, oxendazole, oxibendazole, albendazole, ricobendazole and luxabendazole), Ivermectin, and antimicrobials such as florfenicol, vitamins such as vitamins insoluble in water. Further active ingredients suitable for use in the present invention are described in WO 2010/01128 A as benzimidazoles and alternative antihelmintic drugs. The active ingredient may also be in the form of pharmaceutically acceptable salts, it may be in amorphous or any polymorphic form, including solvates or hydrates. Preferably, the active ingredient is selected from the group consisting of flubendazole, fenbendazole, florfenicol.

The scope of the present invention covers the use of all active ingredients that are suitable for oral administration to animals, which exhibit solubility in water, which is so low that the typical amount of drinking water for the animal species of interest is not sufficient to allow complete dissolution of the required total amount of active ingredient. Typically, solubility in water of the active ingredient is less than 10 mg/ml at 25° C. Solubility of the drugs can be determined according to a definition shown in the Table 1. The formulation according to present invention is particularly suitable to drugs which are slightly soluble, very slightly soluble or insoluble in water (jointly referred to as "poorly soluble").

TABLE 1

| Definition | Parts of solvent required for one part of solute |
| --- | --- |
| Very soluble | <1 |
| Freely soluble | 1-10 |
| Soluble | 10-30 |
| Sparingly soluble | 30-100 |
| Slightly soluble | 100-1000 |
| Very slightly soluble | 1000-10,000 |
| Insoluble | >10,000 |

The formulation of the present invention comprises the at least one active ingredient in an amount of 1 to 90 wt. %, preferably 3-30 wt. %, most preferably 5-15%, relative to the total weight of the formulation of the present invention.

The median particle size of the active ingredient is typically less than 10 microns, preferably less than 5 microns and more preferably less than 3.5 microns and most preferably around 2 microns. It is typically more than 0.01 microns, preferably more than 0.1 microns.

The desired particle sizes can be obtained by means of standard milling procedures such as ball milling jet milling, rotor stator colloid milling and the like as described in greater detail in WO 2007/144362 A.

(c) Thickener Combination

Another essential element of the present invention is the presence of a thickener combination. Said thickener combination is characterized by the presence of at least one thickener selected from the groups A, B, C or D. Preferably said thickener combination is characterized by the presence of at least two different thickeners, wherein among the at last two thickeners at least two are selected from groups A, B, C or D, respectively. Most preferably said thickener combination is characterized by the presence of at least three different thickeners, wherein among the at least three thickeners at least one is selected from groups A, B, C or D, respectively.

Group A thickeners are cellulose derivatives, such as methyl cellulose, ethyl cellulose, hydroxyethyl cellulose, sodium carboxymethylcellulose, calcium carboxymethylcellulose hydroxypropyl cellulose, hydroxypropyl methyl cellulose, preferably sodium carboxymethyl cellulose.

Group B thickeners are non-cellulosic polysaccharide thickeners such as xanthan gum, arabic gum, acacia gum, agar, alginates, carrageenan (lambda, iota and kappa), gellan gum, gum tragacanth, karaya, Inulin, konjac glucomannan, pectin, pullulan, seed gum, starch, chitin and chitosan, and the like, preferably xanthan gum and carrageenan.

Group C thickeners are cross-linked polyacrylic acid polymers, such as carbomers. Typical commercially available Group C thickeners are the Carbopol® family of the Lubrizol Corporation and the Acrysol® series of the Dow Chemical Corporation.

Group D thickeners are hydrocolloidal hydrated silicates, such as potassium (K), sodium (Na), calcium (Ca), and aluminum (Al) bentonite, montmorillonite, hectorite, saponite, beidelite and/or sauconite and synthetic amorphous silicates, preferably aluminum bentonite.

Further information on the thickeners of groups A and B can be found in the textbooks "Food Stabilizers, Thickeners and Gelling Agents" by A. (meson (Ed.), Wiley-Blackwell, 2010 and "Biopolymers from Renewable Sources" by D. L. Kaplan (Ed.), Springer, 1998. Information on thickeners of all three groups A, B and C is found in the "Handbook of Industrial Water Soluble Polymers" by P. A. Williams (Ed.), Blackwell, 2007. In particular, Section 2 of this reference describes polymers that can be used as thickeners of groups A and B. Similarly, Section 3 of this reference describes acrylic polymer thickeners that are suitable for use as thickeners of group C. Thickeners of group D are described in Section 3.1 of "Additives for Coatings", J. Bielemann (Ed.), Wiley-VCH, 2000/2001. This latter reference furthermore contains additional information on suitable thickeners of group A in its Section 3.2.1.

It is possible to use more than one thickener of one or more of the above Groups A, B, C and D. For instance, the use of two thickeners of group A in the absence of other thickeners is possible in accordance with the invention. Similarly, the use of two thickeners of group B in the absence of other thickeners, or the use of two thickeners of group C in the absence of other thickeners, or the use of two thickeners of group D in the absence of other thickeners is also possible in accordance with the present invention. Similarly, it is possible to use additional thickeners of other types. This, however, is not necessary according to the present invention. The effects of the present invention can be achieved using the thickener combination comprising at least one thickener selected from the Groups A, B, C and D.

Total amount of the thickeners can vary from 0.1 wt. % to 10 wt. %, preferably 0.2 wt. % to 7 wt. %, most preferably from 0.4 to 5 wt. % based on the total weight of the formulation.

Within the above limits of the total amount of thickeners, the formulation of the present invention comprises 0 to 10 wt. % of thickener of Group A, preferably 1 to 5 wt. % of thickener of Group A, 0 to 5 wt. % of thickener of Group B, preferably 0.05 to 1 wt. % of thickener of Group B, 0 to 5 wt. % of thickener of Group C, preferably 0.05 to 2 wt. % of thickener of Group C, 0 to 10 wt. % of thickener of Group D, preferably 0.05 to 5 wt. % of thickener of Group D, each relative amount being based on the total weight of the formulation of the present invention.

(d) Solvent

The formulation of the present invention preferably contains one or more solvents other than water. At least one of these solvents is preferably selected from the group consisting of N-methyl pyrrolidone, pyrrolidone, polyethylene glycol, propylene glycol, glycerol formal, isosorbide dimethyl ether, ethanol, dimethyl sulfoxide, tetrahydrofurfuryl alcohol, and glycerol. Preferred solvent are propylene glycol and glycerol.

Said one or more solvents is/are present in the formulation of the invention in a relative amount of 0 to 50 wt. % relative to the total amount of the formulation, preferably 5-30 wt. %, most preferably 10-20 wt. %.

(e) Further Optional Ingredients

The formulation of the present invention may comprise further ingredients. Preferably, the formulation comprises one or more ingredients selected from acidifying agents, chelating agents, preservatives.

(e-1) Acidifying Agents

Possible acidifying agents are selected from pharmaceutically acceptable anorganic or organic acids. Anorganic acids include e.g. hydrochloric, sulphonic, phosphonic acid etc. Organic acid may can be selected form any of organic carboxylic acid, preferably an aliphatic organic carboxylic acid having 3-20 carbon atoms, for example, tartaric, malic, succinic, glutaric, glutamic, maleic, mandelic, citric, alginic, asparaginic, ascorbinic, stearic, tosylic, besylic, salicylic, lactic, benzoic, acetic acid and the like. The preferred acidifying agent is citric acid, in particular in the form of citric acid hydrate.

The relative amount of the acidifying agent is preferably such that the pH of the formulation is within the range of 3 to 7, preferably from 4 to 5.

(e-2) Chelating Agents

The formulation of the present invention preferably contains one or more pharmaceutically acceptable chelating agents, such as EDTA and cyclodextrins. Most preferably the chelating agent is EDTA, especially in its disodium form.

The relative amount of the chelating agent is preferably 0.001 to 0.3 wt % relative to total amount of the formulation (e-3) Preservatives Preferably, the formulation of the invention also contains at least one preservative. Said preservative is preferably selected from the group consisting of parabenes (p-hydroxy benzoates) such as methylparaben ethylparaben, propylparaben, and butylparaben; alkali metal benzoates and/or sorbates. Most preferred are methyl paraben and sodium benzoate, potassium sorbate. Particularly preferred is the use of a combination of methylparaben with sodium benzoate or potassium sorbate.

The one or more preservative(s) is/are preferably present in a relative amount of 0.01 to 1 wt. %, more preferably 0.2 to 0.7 wt. %, relative to the total amount of the formulation.

(e-4) Absence of Oil

According to one aspect of the invention, the formulation does not contain oil or lipid substance, specifically vegetable oils. It is known that lipids, such as oils are susceptible to oxidation. Therefore in the preparations containing oils antioxidants such as BHA, BHT has to be added to achieve desired stability of the preparations. It is reported that BHA and BHT may be implicated in many health risks, including cancer and carcinogenesis and due to these safety concerns the use of such antioxidants should be avoided. Due to the absence of oil, it is possible to obtain stable formulations where the use of anti-oxidative preservatives can be omitted. This, in turn, makes the formulation of the present invention more economical and less risky to health. Therefore, in a particularly preferred embodiment of the present invention, the formulation contains neither an oil or lipid substance, nor an anti-oxidative preservative such as BHT or BHA.

(e-5) Absence of Surfactants

It is known that surfactants may be acutely irritating or damaging to the intestinal mucosa and may provoke diarrhea and growth retardation therefore the use of surfactants in high quantities should be avoided. Another drawback of surfactants is their influence on permeability of the drug which may result in higher toxicity of the drug. In a preferred embodiment of the present invention, the formulation omits the use of surfactants; thus all the abovementioned drawbacks are avoided.

(f) Water

The formulation of the present invention also comprises water. In principle, any water quality suitable for feeding to animals can be used. For cost reasons, normal tab water is preferably used.

The formulation of the invention contains 1 to 90 wt. %, preferably 40 to 80 wt % relative to the total amount of the formulation.

(g) Preferred Formulation Embodiments

The present invention pertains also to the following preferred formulation embodiments:

Formulation Embodiment 1

Formulations wherein the active ingredient is selected from flubendazole, fenbendazole and florfenicol and the thickener combination consists of two thickeners, one of which being selected from any one of groups A, B, C and D and the other thickener being selected from the groups A, B, C and D other than the group, from which the first thickener is selected.

Formulation Embodiment 2

Formulations wherein the active ingredient is selected from flubendazole and the thickener combination consists of three thickeners, one of which being selected from any one of groups A, B, C and D, the second thickener being selected from the groups A, B, C and D other than the group, from which the first thickener is selected, and the third thickener being selected from the groups A, B, C and D other than the two groups, from which the first and second thickeners are selected.

Formulation Embodiment 3

Formulations wherein the thickener combination includes two, three or more thickeners selected from sodium carboxymethyl cellulose, xanthan gum, carrageenan, carbomer, and aluminum bentonite.

Formulation Embodiment 3a

Formulations wherein the thickener combination includes two or three thickeners selected from sodium carboxymethyl cellulose, xanthan gum, carbomer.

Formulation Embodiment 4a

Formulations according to formulation embodiment 1, wherein the thickeners are selected only from the thickeners listed with respect to formulation embodiment 3 or 3a.

Formulation Embodiment 4b

Formulations according to formulation embodiment 2, wherein the thickeners are selected only from the thickeners listed with respect to formulation embodiment 3 or 3a.

Formulation Embodiment 5a

Formulations according to formulation embodiment 1, which contain a solvent selected from propylene glycol, glycerol and mixtures thereof.

Formulation Embodiment 5b

Formulations according to formulation embodiment 2, which contain a solvent selected from propylene glycol, glycerol and mixtures thereof.

Formulation Embodiment 5c

Formulations according to formulation embodiment 3 or 3a, which contain a solvent selected from propylene glycol, glycerol and mixtures thereof.

Formulation Embodiment 5d

Formulations according to formulation embodiment 4a, which contain a solvent selected from propylene glycol, glycerol and mixtures thereof.

Formulation Embodiment 5e

Formulations according to formulation embodiment 4b, which contain a solvent selected from propylene glycol, glycerol and mixtures thereof.

Formulation Embodiment 6a

Formulations according to formulation embodiment 1, which neither contain oil nor anti-oxidative preservative.

Formulation Embodiment 6b

Formulations according to formulation embodiment 2, which neither contain oil nor anti-oxidative preservative.

Formulation Embodiment 6c

Formulations according to formulation embodiment 3 or 3a, which neither contain oil nor anti-oxidative preservative.

Formulation Embodiment 6d

Formulations according to formulation embodiment 4a, which neither contain oil nor anti-oxidative preservative.

Formulation Embodiment 6e

Formulations according to formulation embodiment 4b, which neither contain oil nor anti-oxidative preservative.

Formulation Embodiment 6f

Formulations according to formulation embodiment 5a, which neither contain oil nor anti-oxidative preservative.

Formulation Embodiment 6g

Formulations according to formulation embodiment 5b, which neither contain oil nor anti-oxidative preservative.

Formulation Embodiment 6h

Formulations according to formulation embodiment 5c, which neither contain oil nor anti-oxidative preservative.

Formulation Embodiment 6i

Formulations according to formulation embodiment 5d, which neither contain oil nor anti-oxidative preservative.

Formulation Embodiment 6j

Formulations according to formulation embodiment 5e, which neither contain oil nor anti-oxidative preservative.

Formulation Embodiment 7a

Formulations according to formulation embodiment 1, which do not contain surfactant.

Formulation Embodiment 7b

Formulations according to formulation embodiment 2, which do not contain surfactant.

Formulation Embodiment 7c

Formulations according to formulation embodiment 3 or 3a, which do not contain surfactant.

Formulation Embodiment 7d

Formulations according to formulation embodiment 4a, which do not contain surfactant.

Formulation Embodiment 7e

Formulations according to formulation embodiment 4b, which do not contain surfactant.

Formulation Embodiment 7f

Formulations according to formulation embodiment 5a, which do not contain surfactant.

Formulation Embodiment 7g

Formulations according to formulation embodiment 5b, which do not contain surfactant.

Formulation Embodiment 7h

Formulations according to formulation embodiment 5c, which do not contain surfactant.

Formulation Embodiment 7i

Formulations according to formulation embodiment 5d, which do not contain surfactant.

Formulation Embodiment 7j

Formulations according to formulation embodiment 5e, which do not contain surfactant.

Formulation Embodiment 7k

Formulations according to formulation embodiment 6a, which do not contain surfactant.

Formulation Embodiment 7l

Formulations according to formulation embodiment 6b, which do not contain surfactant.

Formulation Embodiment 7m

Formulations according to formulation embodiment 6c, which do not contain surfactant.

Formulation Embodiment 7n

Formulations according to formulation embodiment 6d, which do not contain surfactant.

Formulation Embodiment 7o

Formulations according to formulation embodiment 6e, which do not contain surfactant.

Formulation Embodiment 7p

Formulations according to formulation embodiment 6f, which do not contain surfactant.

Formulation Embodiment 7q

Formulations according to formulation embodiment 6g, which do not contain surfactant.

Formulation Embodiment 7r

Formulations according to formulation embodiment 6h, which do not contain surfactant.

Formulation Embodiment 7s

Formulations according to formulation embodiment 6i, which do not contain surfactant.

Formulation Embodiment 7t

Formulations according to formulation embodiment 6j, which do not contain surfactant.

(h) Method for Manufacturing the Formulation

The formulation of the invention can be manufactured by a process, wherein a mixture of thickener combination and water is formed, and wherein this mixture is subsequently combined with the active ingredient.

In a preferred process, the active ingredient is mixed with the solvent prior to its combination with the mixture containing the thickener combination and water. This step can be carried out at temperatures from 20° C. to 65° C., preferably from 30° C. to 60° C.

According to another preferred embodiment of the invention, the process includes a step of adding at least one preservative to the mixture of thickener combination and water, prior to the combination with active ingredient (the active ingredient optionally being in the form of a mixture with solvent).

According to a yet further embodiment of the invention, the individual thickeners of groups A, B, C and D are incorporated separately in a step-wise approach, wherein the relative order of incorporation is not limited.

It is preferred that each mixture is homogenized prior to the subsequent addition or mixing step. Homogenization can be carried out suitably with means such as a rotor stator or a high pressure homogenizer. Homogenization is preferably carried out until suitable homogeneity level is achieved. Suitable methods of homogenization are described in EP 0 727 996 B.

According to further preferred embodiment of the invention, the process includes the following steps:

Preservative, preferably sodium benzoate, is added to water. The resulting mixture is stirred until a clear solution is obtained. To the obtained solution thickener of a first group, for instance group B and preferably xanthan gum, is added, the mixture is stirred and homogenized. Then thickener of a second group, for instance group A and preferably sodium carboxymethylcellulose, is added, the mixture is stirred and homogenized. Finally thickener of a third group, for instance group C and preferably carbomer, is added and the mixture is stirred and homogenized to obtain a mixture. To the obtained mixture chelating agent, preferably disodium EDTA, acidifying agent, preferably citric acid monohydrate, and further preservative, preferably methyl parahydroxybenzoate, is added, the mixture is stirred and heated, preferably to 80-90° C.

Then the mixture is cooled, preferably to 30-60° C. most preferably to 50-60° C. Active ingredient, preferably flubendazole, is dispersed in solvent, preferably propylene glycol, homogenized and added to the cooled mixture. The resulting mixture is stirred, homogenized and cooled to room temperature.

(i) Uses of the Formulation of the Invention

The formulation of the present invention is designed to allow convenient administration of the water-insoluble active ingredient to animals.

The formulation of the invention is typically provided in a concentrated form (having a active ingredient content of 1 to 90 wt. %, preferably 3-30 wt %, more preferably 5-15 wt. %). Said concentrated form is normally diluted with drinking water prior to use. The active ingredient content of the resulting diluted formulation is from 0.0005 to 1 wt. %. The above-mentioned relative amounts of the other components of the formulation of the invention (except water, of course) are reduced accordingly (lower limiting values to be reduced by a factor of 2000; upper limiting values to be reduced by a factor of 90).

The species of animals, to which the formulation can be administered, include pigs, all categories of chickens and other poultry, cattle and fish.

Administration can be effected for medical (therapeutic or prophylactic) purposes. Nonmedical (e.g. commercial) purposes are also conceivable.

Medical uses include the administration of antiparasitic active agents to poultry, pigs, cattle or fish for the treatment or prophylaxis of parasitic infections. Other medical uses include the administration of antimicrobial agents to pigs, cattle or fish for the treatment or prophylaxis of microbial infections. Further medical uses include the administration of poorly water soluble vitamins to poultry, pigs, cattle or fish for the treatment or prophylaxis of hypovitaminosis.

Precise dosage, administration frequency and duration can be determined by the skilled person based on the specific circumstances and objectives of the treatment. For instance, administration of antiparasitic active ingredients to poultry by means of the formulation of the present invention can preferably be effected for treatment periods of 2 to 24 hours on one to six consecutive days.

Non-medical uses according to the present invention include the administration of the formulation of the present invention containing poorly water soluble vitamins to poultry, pigs, cattle or fish for weight gain of the animals.

(j) Examples

(j-1) Inventive Example

0. Flubendazole Peroral Dispersion-Composition

| Ingredients | Amounts per 1 g (one packaging 100 g) |
|---|---|
| Active ingredient | |
| Flubendazole | 100 mg |
| Excipients | |
| Blanose 9M 31 X FPh | 20.0 mg |
| Xanthan gum (Keltrol F) | 1.0 mg |
| Citric acid hydrate | 5 mg |
| Carbopol 971 NF | 2 mg |
| Disodium EDTA | 0.1 mg |
| Methyl parahydroxybenzoate | 4 mg |

-continued

| Ingredients | Amounts per 1 g (one packaging 100 g) |
|---|---|
| Propylene glycol | 150 mg |
| Purified water | 712.9 mg |
| Sodium benzoate | 5.0 mg |

2. Technological Process

F1: To purified water sodium benzoate is added, the mixture is stirred until a clear solution is obtained. To the obtained solution xanthan gum is added, the mixture is stirred and homogenized. Then Blanose 9M 31×FPh is added, the mixture is stirred and homogenized. Finally Carbopol 971 NF is added and the mixture is stirred and homogenized to obtain the F1 phase.

F2: To F1 Disodium EDTA, citric acid monohydrate and Methyl parahydroxybenzoate is added, the mixture is stirred and heated to 85° C., then the mixture is cooled to 55° C.

F3: Flubendazole is dispersed in propylene glycol, homogenized and added to F2. The obtained mixture is stirred, homogenized and cooled to room temperature.

(j-1a) Inventive Example

1. Flubendazole Peroral Dispersion-Composition

| Ingredients | Amounts per 1 g (one packaging 100 g) |
|---|---|
| Active ingredient | |
| Flubendazole | 100 mg |
| Excipients | |
| Blanose 9M 31 X FPh | 25.0 mg |
| Xanthan gum (Keltrol F) | 1.0 mg |
| Citric acid hydrate | 5 mg |
| Carbopol 971 NF | 2 mg |
| Methyl parahydroxybenzoate | 4 mg |
| Propylene glycol | 150 mg |
| Purified water | 708.0 mg |
| Sodium benzoate | 5.0 mg |

2. Technological Process

F1: To purified water sodium benzoate is added, the mixture is stirred until a clear solution is obtained. To the obtained solution xanthan gum is added, the mixture is stirred and homogenized. Then Blanose 9M 31×FPh is added, the mixture is stirred and homogenized. Finally Carbopol 971N homogenized to obtain the F1 phase.

F2: To F1 citric acid monohydrate and Methyl parahydroxybenzoate is added, the mixture is stirred and heated to 85° C., then the mixture is cooled to 55° C.

F3: Flubendazole is dispersed in propylene glycol, homogenized and added to F2. The obtained mixture is stirred, homogenized and cooled to room temperature.

(j-1b) Inventive Example

1. Flubendazole Peroral Dispersion-Composition

| Ingredients | Amounts per 1 g (one packaging 100 g) |
|---|---|
| Active ingredient | |
| Flubendazole | 100 mg |
| Excipients | |
| Blanose 9M 31 X FPh | 20.0 mg |
| Xanthan gum (Keltrol F) | 1.0 mg |
| Citric acid hydrate | 5 mg |
| Carbopol 971 NF | 2.5 mg |
| Disodium EDTA | 0.1 mg |
| Methyl parahydroxybenzoate | 4 mg |
| Glycerol | 150 mg |
| Purified water | 712.9 mg |
| Sodium benzoate | 5.0 mg |

1. Technological Process

F1: To purified water sodium benzoate is added, the mixture is stirred until a clear solution is obtained. To the obtained solution xanthan gum is added, the mixture is stirred and homogenized. Then Blanose 9M 31×FPh is added, the mixture is stirred and homogenized. Finally Carbopol 971 NF is added and the mixture is stirred and homogenized to obtain the F1 phase.

F2: To F1 Disodium EDTA, citric acid monohydrate and Methyl parahydroxybenzoate is added, the mixture is stirred and heated to 85° C., then the mixture is cooled to 55° C.

F3: Flubendazole is dispersed in glycerol, homogenized and added to F2. The obtained mixture is stirred, homogenized and cooled to room temperature.

(j-2) Comparative Example

A flubendazole formulation prepared in accordance with the teaching of EP 1 214 052 A (Example 1), commercially available as Solubenol 100 mg/g Oral Emulsion

| Ingredients | Amounts per 1 g (one packaging 100 g) |
|---|---|
| Active ingredient | |
| Flubendazole | 100 mg |
| Excipients | |
| Sunflower oil | 300 mg |
| gum arabic | 150 mg |
| Monoglyceride citrate | 20 mg |
| Xanthan gum | 2.5 mg |
| Citric acid monohydrate | 5 mg |
| Disodium EDTA | 0.1 mg |
| Propylene glycol | 50 mg |
| Propyl parahydroxybenzoate | 4 mg |
| Methyl parahydroxybenzoate | 4 mg |
| Butylhydroxytoluene | 0.2 mg |
| Sodium hydroxide | 10 mg |
| Purified water | 355 mg |

(j-3) Evaluation

Subsequent evaluation of the obtained formulation revealed that the formulation according to the present invention exhibits a greater stability than the formulation of the comparative example under the following test conditions:

Physical stability at storage conditions: 40° C. in closed container

| | Testing time | |
|---|---|---|
| Formulation | 1 month | 2 months |
| Comparative Example | System separated in two phases | System separated in two phases |
| Example 1 | Homogenous system | Homogenous system |

The formulation of the present invention is economical, particularly stable on storage and water dilution and does not show sedimentation. It is particularly well suited for administration to animals via their drinking water in connection with the rearing of said animals.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention claimed is:

1. A formulation for administration to drinking water of animals comprising a poorly water soluble active ingredient, a thickener combination and water,
wherein the active ingredient exhibits a particle size within the range of from 0.01 microns to 10 microns; and
wherein the thickener combination comprises at least three thickeners selected from the following groups A, B, C and D:
A. cellulose derivatives comprising sodium carboxy methyl cellulose,
B. non-cellulosic polysaccharide thickeners comprising xanthan gums, and/or carrageenan,
C. cross-linked polyacrylic acid polymers comprising carbomers; and
D. hydrocolloidal hydrated silicates comprising aluminum bentonite; and
wherein the formulation is in concentrated form such that the active ingredient content is 1 to 90 wt. % and wherein no oil and no surfactant is contained in the formulation.

2. The formulation according to claim 1, further comprising a solvent selected from the group consisting of N-methyl pyrrolidone, pyrrolidone, polyethylene glycol, propylene glycol, glycerol formal, isosorbide dimethyl ether, ethanol, dimethyl sulfoxide, tetrahydrofurfuryl alcohol, and glycerol.

3. A process for manufacturing the formulation according to claim 1, comprising the step of forming a mixture of thickener combination and water; followed by combining this mixture with the active ingredient.

4. The process according to claim 3, wherein the active ingredient is mixed with solvent prior to its combination with the mixture containing the thickener combination and water.

5. The process according to claim 3, wherein the process includes a step of adding at least one preservative to the mixture of thickener combination and water, prior to the combination with active ingredient.

6. A method for the treatment of parasitic infections, microbial infections or hypovitaminosis in an animal by administering to said animal a formulation of claim 1.

7. A method for increasing growth of animals by administering to said animals a formulation according to claim 1.

8. The formulation according to claim 1, wherein the active ingredient exhibits a particle size within the range of from 0.1 microns to 5 microns.

9. The formulation according to claim 1, further comprising a solvent selected from the group consisting of N-methyl pyrrolidone, pyrrolidone, polyethylene glycol, propylene glycol, glycerol formal, isosorbide dimethyl ether, ethanol, dimethyl sulfoxide, tetrahydrofurfuryl alcohol, and glycerol.

* * * * *